United States Patent
Van Der Wilk et al.

(10) Patent No.: US 11,819,437 B2
(45) Date of Patent: Nov. 21, 2023

(54) ANKLE FOOT ORTHOSIS

(71) Applicant: Ottobock SE & Co. KGaA, Duderstadt (DE)

(72) Inventors: Anna Sibylla Dymphna Van Der Wilk, Haren (NL); Roy Reints, Groningen (NL); Gijsbertus Jacob Verkerke, Glimmen (NL); Juha Markus Hijmans, Haren (NL); Klaas Postema, Oldenzaal (NL)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 1209 days.

(21) Appl. No.: 16/465,098

(22) PCT Filed: Dec. 22, 2016

(86) PCT No.: PCT/EP2016/082450
§ 371 (c)(1),
(2) Date: May 29, 2019

(87) PCT Pub. No.: WO2018/113982
PCT Pub. Date: Jun. 28, 2018

(65) Prior Publication Data
US 2019/0298564 A1    Oct. 3, 2019

(51) Int. Cl.
*A61F 5/01*    (2006.01)

(52) U.S. Cl.
CPC .......... *A61F 5/0127* (2013.01); *A61F 5/0111* (2013.01); *A61F 2005/0155* (2013.01);
(Continued)

(58) Field of Classification Search
CPC ...... A61F 2005/0155; A61F 2005/0158; A61F 2005/0179; A61F 2005/0188; A61F 2005/0197; A61F 5/0111; A61F 5/0127
See application file for complete search history.

(56) References Cited

U.S. PATENT DOCUMENTS

| 5,807,255 A | 9/1998 | Yokota et al. |
| 8,696,764 B2 | 4/2014 | Hansen et al. |

(Continued)

FOREIGN PATENT DOCUMENTS

| CN | 101912320 B | 10/2012 |
| CN | 105616113 A | 6/2016 |

(Continued)

OTHER PUBLICATIONS

International Search Report for International Application No. PCT/EP2016/082450, dated Sep. 21, 2017, 3 pages.

*Primary Examiner* — Keri J Nelson
(74) *Attorney, Agent, or Firm* — HOLLAND & HART LLP

(57) ABSTRACT

An ankle foot orthosis having a lower leg element, a foot element being pivotably coupled to the lower leg element around a pivot axis, and a first energy storing unit being adapted such that moving the foot element relative to the lower leg element in dorsiflexion direction from a position in which the amount of energy stored in the first energy storing unit is minimal loads the first energy storing unit with energy. The first energy storing unit is adapted such that the amount of energy stored in the first energy storing unit is increased by moving the foot element relative to the lower leg element in a plantar flexion direction from a first position in which the amount of energy stored in the first energy storing unit is minimal into a second position and moving the foot element relative to the lower leg element in dorsiflexion direction from the second position back into the first position.

14 Claims, 5 Drawing Sheets

(52) U.S. Cl.
CPC ............... *A61F 2005/0158* (2013.01); *A61F 2005/0179* (2013.01); *A61F 2005/0188* (2013.01)

(56) References Cited

U.S. PATENT DOCUMENTS

| | | |
|---|---|---|
| 2004/0064195 A1 | 4/2004 | Herr |
| 2008/0287847 A1 | 11/2008 | Pansiera |
| 2013/0046218 A1 | 2/2013 | Wiggin et al. |
| 2014/0330393 A1 | 11/2014 | Ward et al. |
| 2015/0150694 A1 | 6/2015 | Pusch et al. |

FOREIGN PATENT DOCUMENTS

| | | |
|---|---|---|
| CN | 205359728 U | 7/2016 |
| WO | 03013401 A1 | 2/2003 |
| WO | 2008048658 A2 | 4/2008 |

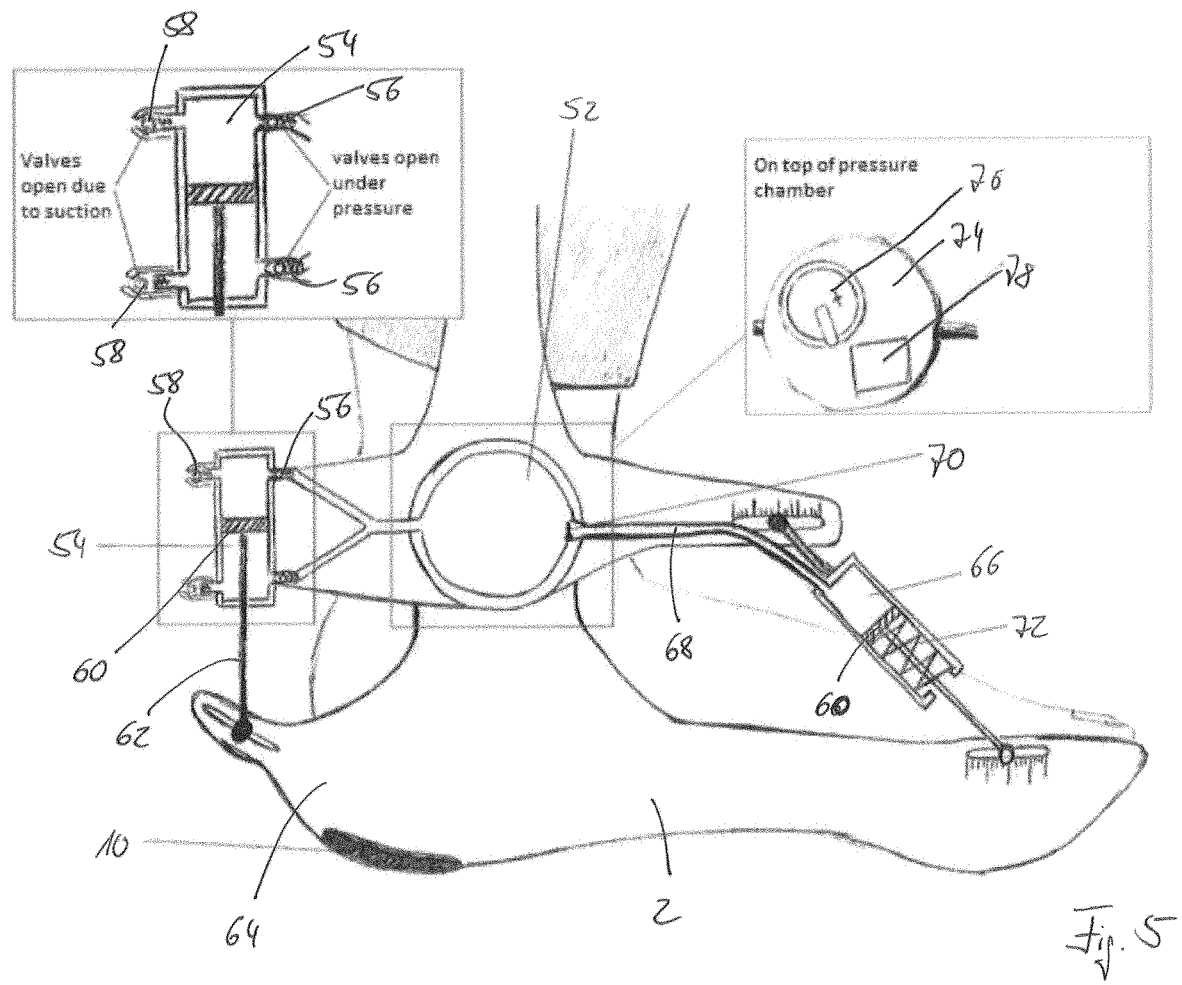

ANKLE FOOT ORTHOSIS

CROSS REFERENCE TO RELATED APPLICATION

This application is a U.S. national entry application from PCT International Patent Application No. PCT/EP2016/082450, filed 22 Dec. 2018, and entitled ANKLE FOOT ORTHOSIS, the disclosure of which is incorporated, in its entirety, by this reference.

TECHNICAL FIELD

The invention relates to an ankle foot orthosis comprising a lower leg element, a foot element being pivotably coupled to the lower leg element and a first energy storing unit being adapted such that moving the foot element relative to the lower leg element in dorsiflexion direction from a position in which the amount of energy stored in the first energy storing unit is minimal loads the first energy storing unit with energy. Dorsiflexion means that the angle between the foot element and the lower leg element decreases. Plantar flexion means that the angle between the foot element and the lower leg element increases.

Such an ankle foot orthosis is known from US 2013/0046218 A1.

BACKGROUND

Ankle foot orthoses can improve, but also hamper the performance of daily life activities in people with flaccid paresis of the ankle muscle. The main activity throughout the day is gait. A gait cycle can be divided into four different phases. The cycle starts with a heel strike of the foot. Once the heel of the foot has touched the ground a first phase follows which is called "controlled plantar flexion". This happens because after the heel has touched the ground the full foot is low-erect until the maximum plantar flexion angle is reached after which the complete foot lies flatly on the ground. In an ankle foot orthosis known from U.S. Pat. No. 8,696,764 B2, US 2004/0064195 A1 and the already mentioned US 2013/0046218 A1 in this controlled plantar flexion phase no energy is stored in the first energy storing unit.

After this first phase there is the so-called controlled dorsiflexion phase. Here a certain range of motion of the ankle joint between the foot element and the lower leg element is needed so that the tibia inclines in a controlled manner. The controlled dorsiflexion phase ends after the heel is lifted from the ground and maximum dorsiflexion angle is reached. The maximum dorsiflexion angle means that the angle between the foot element and the lower leg element is minimal. The value of the angle between the foot element and the lower leg element at the maximum dorsiflexion angle can change from step to step. At this point the third phase, the so-called "powered plantar flexion phase" begins. In this phase power is generated at the ankle to propel the body forward by an active plantar flexion motion and moment. Orthoses known from prior art can store energy in the first energy storing unit during the controlled dorsiflexion phase and release it during powered plantarflexion phase to generate the necessary power. The first energy storing unit in these cases can be an elastic element such as a spiral spring or a block made from an elastic material such as rubber.

After the "toe-off" when the foot has completely left the floor the swing phase starts. At the end of the swing phase the heel of the foot touches the ground and one gait cycle is completed.

In order to provide a naturally looking and convenient gait cycle with an ankle foot orthosis having only one energy storing unit the amount of energy stored in the first energy storing unit in the swing phase is minimal or at least very low. Otherwise the first phase of the gait cycle after the heel strike, the "controlled plantar flexion" would be controlled, since the first energy storing unit during this movement would release at least some of the stored energy. Hence, usually no energy is stored in the first energy storing unit during swing phase. The first energy storing unit usually has a so-called "zero position" which can defined to be the angle between the foot element and the lower leg element at which the amount of energy stored in the first energy storing unit is minimal. It has to be noted that the amount of energy is not necessarily zero.

With an ankle foot orthosis which has only one first energy storing unit it is only possible to store energy and to load the energy storing unit during a dorsiflexion movement beyond this zero position. This loading of the first energy storing unit thus has to take place during the controlled dorsiflexion phase. Usually, the zero position of an ankle foot orthosis according to prior art is at an angle of roughly 90° between the foot element and the lower leg element. This corresponds to the angle between the two elements during standing. Hence, the loading of the first energy storing unit starts once the angle between the foot element and the lower leg element decreases below this zero position. Consequently the energy stored in this first energy storing unit can be released during the powered plantar flexion phase only until the angle of the zero position is reached. It is simply not possible to release any more energy from the first energy storing unit beyond this zero position. However, the angle between the foot element and the lower leg element of a healthy leg during a normal gait cycle usually is larger than this zero position in both controlled plantar flexion phase and powered plantar flexion phase. Hence, with an ankle foot orthosis according to the prior art, a normally looking gait cycle is not achievable.

SUMMARY

It is thus an object of the present invention to overcome this drawback of the prior art orthoses.

The invention solves this problem by an ankle foot orthosis wherein the first energy storing unit is adapted such that the amount of energy stored in the first energy storing unit is increased by
first moving the foot element relative to the lower leg element in plantar flexion direction from a first position in which the amount of energy stored in the first energy storing unit is minimal into a second position and
afterwards moving the foot element relative to the lower leg element in dorsiflexion direction from the second position back into the first position.

This does not necessarily mean that during each of the described movements the amount of energy that is stored in the first energy storing unit is increased. But moving the foot element in plantar flexion direction and moving back in dorsiflexion direction in combination increases the energy stored. An ankle foot orthosis according to the present invention may have only one energy storing unit which is called "first" energy storing unit even though it might be the only energy storing unit of the orthosis. However, an ankle foot orthosis according to the present invention may also have more than one energy storing unit, one of which is called "first" energy storing unit.

During a normal gait cycle the angle between the foot element and the lower leg element first increases in the controlled plantarflexion phase. Afterwards in the controlled dorsiflexion phase the angle decreases again. Hence, the foot element is first moved relative to the lower leg element in plantarflexion direction from a first position into a second position. This takes place in the controlled plantarflexion phase. Afterwards the foot element is moved relative to the lower leg element in dorsiflexion direction from the second position back into the first position and usually beyond this position. This takes place in the controlled dorsiflexion phase. At this point when the angle between the foot element and the lower leg element passes the first position, the amount of energy stored in the first energy storing unit is increased compared to the amount of energy stored in the first energy storing unit before these two movements of the foot element relative to the lower leg element have been performed. Since the amount of energy stored in the first energy storing unit is minimal in the first position, this first position could be called "zero position". Moving the foot element out of the "zero position" which corresponds to a certain angle between the foot element and the lower leg element in plantarflexion direction and back to the same first position in dorsiflexion direction increases the amount of energy stored in the first energy unit. This means that the first position is no longer a "zero position" after these two movements have been performed since the amount of energy stored in the first energy storing unit is no longer minimal.

It has to be noted that the first position in which the amount of energy stored in the first energy storing unit is minimal not necessarily coincides with a neutral position of the ankle foot orthosis. This "neutral position" of the orthotic device is achieved in the swing phase when no external pressures and/or forces act on the orthosis. It is possible that this neutral position does not coincide with a "zero position" of the first energy storing unit. This can in particular happen when there are further energy storing units such as spring elements acting against the first energy storing unit.

Preferably the orthosis according to the present invention comprises a release mechanism in order to release energy stored in the first energy storing unit so that a desired angle between the foot element and the lower leg element is a "zero position" again and can be used as a first position according to the present invention.

In a preferred embodiment of the present invention, the first energy storing unit is adapted such that the amount of energy stored in the first energy storing unit after the foot element is moved from the first position into the second position is still minimal. This means that this movement does not affect the amount of energy stored in the first energy storing unit. In this case also the second position is a "zero position" of the first energy storing unit since also in this second position the amount of energy stored in the first energy storing unit is minimal. In other words, moving the foot element relative to the lower leg element in plantarflexion direction from the first position in which the amount of energy stored in the first energy storing unit is minimal into the second position shifts the "zero position" of the first energy storing unit. After this movement the foot element is in the second position relative to the lower leg element but still the amount of energy stored in the first energy storing unit is minimal which is the definition of a "zero position". Hence, the angle between the foot element and the lower leg element that is identified to be a "zero position" is increased during this movement.

Let's assume the first position is defined to be an angle of 90° between the foot element and the lower leg element. The first position is a zero position of the first energy storing unit which means that the amount of energy stored in the first energy storing unit is minimal. The first energy storing unit will be loaded once the foot element will be moved relative to the lower leg element in a dorsiflexion direction beyond this first position. Hence, in order to load the first storing unit the angle between the foot element and the lower leg element has to be smaller than 90°. If now prior to this movement in dorsiflexion direction the foot element is moved relative to the lower leg element in plantar flexion direction to the second position this shifts the zero position, since the amount of energy stored in the first energy storing unit is still minimal. Let's assume this movement in plantar flexion direction is a movement of about 10°. Now the angle between the foot element and the lower leg element is 100° and thus larger than the first position. This angle corresponds to the second position which now is a zero position.

This has the advantage that the first energy storing unit can be loaded once the angle between the foot element and the lower leg element is smaller than 100°. Thus, the loading starts at an earlier stage in the controlled dorsiflexion phase. Due to this earlier loading a larger amount of energy can be stored in the first energy storing unit during the controlled dorsiflexion phase. This larger amount of energy will then be released during the powered plantar flexion phase and it can be released until the angle between the foot element and the lower leg element is the angle corresponding to the second position, in the present example 100° which corresponds to the zero position. This leads to a more naturally looking gait cycle and eases the powered plantar flexion phase.

Preferably the ankle foot orthosis further comprises a second energy storing unit being adapted such that moving the foot element relative to the lower leg element in plantar flexion direction from a position in which the amount of energy is minimal loads the second energy storing unit with energy.

The second energy storing unit thus works the opposite way than the first energy storing unit. Loading of the second energy storing unit takes place during a movement of the foot element relative to the lower leg element in a plantar flexion direction. This means that the angle between the foot element and the lower leg element increases during this movement. As already mentioned this takes place during the controlled plantar flexion and the powered plantar flexion phase.

During the controlled plantar flexion phase after the heel strike of the foot the foot element moves relative to the lower leg element in plantar flexion direction and thus the second energy storing unit is loaded with energy. The second energy storing unit releases the energy at the beginning of the controlled dorsiflexion phase when the angle between the foot element and the lower leg element starts decreasing.

During the powered plantar flexion phase the energy stored in the first energy storing unit is released which usually leads to a movement of the foot element relative to the lower leg element in plantar flexion direction beyond the "zero position" of the second energy storing unit. This zero position is defined to be an angle between the foot element and the lower leg element at which the amount of energy stored in the second energy storing unit is minimal. Passing this position in plantar flexion direction means that the second energy storing unit is loaded with energy. This energy can then be released in a swing phase so that the toe of the wearer of the ankle foot orthosis is lifted since the releasing of the energy stored in the second energy storing unit results in a dorsiflexion motion.

In a preferable embodiment of the present invention the second energy storing unit is adapted such that moving the foot element relative to the lower leg element in dorsiflexion direction from a position in which the amount of energy stored in the second energy storing unit is minimal does not change the amount of energy stored in the second energy storing unit. This corresponds to the shifting of the zero position of the first energy storing unit already described and differs from this only in the direction of the movement of the foot element relative to the lower leg element.

Throughout a gait cycle the zero position of the first energy storing unit will be shifted to the maximum angle between the foot element and the lower leg element that is reached during the respective gait cycle. This maximum angle is reached at the end of a controlled plantar flexion phase of a gait cycle. Correspondingly the zero position of the second energy storing unit in this preferred embodiment of the present invention will be shifted to the minimum angle between the foot element and the lower leg element that corresponds to the end of this controlled dorsiflexion phase when maximum dorsiflexion angle is reached. This means the angle between the foot element and the lower leg element becomes minimal.

It has been proven advantageous that the ankle foot orthosis further comprises a first uncoupling unit that is adapted to uncouple the first energy storing unit from the movement of the foot element relative to the lower leg element, such that moving the foot element relative to the lower leg element does neither loads nor releases energy in or from the first energy storing unit wherein the first energy storing unit is adapted to release the stored energy when the first uncoupling unit uncouples the first energy storing unit.

Once the first uncoupling unit uncouples the first energy storing unit from the movement of the foot element relative to the lower leg element the foot element can be moved freely without loading or releasing any energy in or from the first energy storing unit. Of course, the first uncoupling unit is also adapted to couple the first energy storing unit to the movement of the foot element relative to the lower leg element. In a particularly preferred embodiment of the invention, the zero position of the first energy storing unit gets shifted to that angle between the foot element and the lower leg element at which the first energy storing unit gets coupled to the movement of the foot element relative to the lower leg element again.

When the first energy storing unit is decoupled from the movement of the foot element it will release the energy stored in the energy storing unit. This means that the stored energy will be released unless an external force which can be applied by another element of the orthosis prevents this. In other words the first energy storing unit is no longer capable of keeping the energy stored but will release it as soon as possible.

Preferably the ankle foot orthosis further comprises a second uncoupling unit adapted to uncouple the second energy storing unit from the movement of the foot element relative to the lower leg element such that moving the foot element relative to the lower leg element does neither load nor unload the second energy storing unit wherein the second energy storing unit is adapted to release the stored energy when the second uncoupling unit uncouples the second energy storing unit. Particularly preferable the zero position of the second energy storing unit gets shifted to that angle between the foot element and the lower leg element at which the second energy storing unit gets coupled to the movement again. At the time of uncoupling the energy storing unit, immediately all the energy that was stored in the energy storing unit will be released unless an external force which can be applied by another element of the orthosis prevents this.

Preferably, at least one of the first energy storing unit and the second energy storing unit comprises at least one spring element. With this spring element a mechanically and constructively very easy configuration can be built.

In a preferred embodiment of the invention the at least one spring element of the first energy storing unit has a higher stiffness than the at least one spring element of the second energy storing unit. This is advantageous because the energy stored in the first energy storing unit is used to generate the power necessary for the powered plantar flexion phase. Hence, a lot of energy has to be stored. In contrast the energy stored in the second energy storing unit is used to ease the beginning of the controlled dorsiflexion phase and to lift the foot in the swing phase. To lift the foot in the swing phase only little energy is needed, since there is no load on the foot.

Alternatively, the first energy storing unit and/or the second energy storing unit can comprise a pneumatic or hydraulic system and at least one pressure reservoir to store energy in form of pressure.

Preferably at least one of the first or second uncoupling unit comprises a pawl and a ratchet. This again leads to a very easy construction of the ankle foot orthosis. In order to uncouple one of the energy storing units from the movement of the foot element relative to the lower leg element, it is only necessary to activate the pawl and to disengage it from the ratchet teeth. The foot can then freely move and in order to couple the energy storing unit to the movement again, simply the pawl has to be deactivated so that it engages the teeth of the ratchet. With this disengagement and engagement between the pawl and the ratchet which results in an uncoupling and coupling of the energy storing unit also the corresponding zero position can be reset and shifted to the angle between the foot element and the lower leg element at which the reengagement and thus the coupling took place. Of course, it is also possible to uncouple only one of the first energy storing unit and the second energy storing unit. In this case the respective other energy storing unit is still coupled to the movement of the foot element relative to the lower leg element. Hence, the foot cannot completely freely move relative to the lower leg element since still one energy storing unit is coupled to its movement.

Preferably, the ankle foot orthosis comprises at least one sensor to identify a swing phase of a gait cycle and the orthosis further comprises a control unit to uncouple the first energy storing unit when a swing phase is identified. In one embodiment there are two pressure sensors. One pressure sensor is positioned in the forefoot part to detect whether the toe area of the foot is in contact with the floor. The second sensor is in contact with a rear foot part to detect whether the heel is in contact with the floor. If both sensors detect that their corresponding part of the foot is not in contact with the floor the swing phase is identified.

In a particularly preferred embodiment of the ankle foot orthosis according to the present invention the first energy storing unit can be uncoupled using the first uncoupling unit and the zero position of the second energy storing unit will not be affected at all. A gait cycle with this embodiment will be described now.

In the controlled plantar flexion phase the foot element and the lower leg element are moved relative to each other in plantar flexion direction. For the first energy storing unit and its zero position this means that the zero position is shifted to a larger angle between the foot element and the lower leg element and thus gets shifted in plantar flexion direction. If the movement starts with the minimal amount of energy stored in the first energy storing unit, the amount of energy stays minimal. In other words moving the foot relative to the lower leg element in plantar flexion direction in this case does not change the amount of energy stored in the first energy storing unit. If the movement starts when the amount of energy stored in the first energy storing unit is not minimal, this amount will be decreased during the movement in plantar flexion direction until it is minimal. Any further movement of the foot element relative to the lower leg element in plantar flexion direction will leave the amount of energy unaffected. With this preferred embodiment of the first energy storing unit this happens independently from the particular choice of the second energy storing unit.

For the second energy storing unit the movement in plantar flexion direction means that it will be loaded with energy. At the end of the controlled plantar flexion phase the maximum plantar flexion angle is reached.

Now the controlled dorsiflexion phase starts. The energy stored in the second energy storing unit will be released. At the same time the movement of the foot element and the lower leg element relative to each other in dorsiflexion direction leads to a loading of the first energy storing unit with energy. This ends when the maximum dorsiflexion angle is reached at the end of the controlled dorsiflexion phase. The second energy storing unit is not loaded with any energy and in this particular embodiment its zero position is not changed.

At the end of the controlled dorsiflexion phase when the maximum dorsiflexion angle is reached, powered plantar flexion phase begins. Here, the energy stored in the first energy storing unit is released. It will be released until the angle that corresponds to the zero position is reached when all the energy has been released and the amount of energy stored in the first energy storing unit is minimal. This at least roughly corresponds to the angle at the end of a controlled plantar flexion phase. At the end of the powered plantar flexion phase the toe also leaves the ground and the swing phase starts. The sensors of the ankle foot orthosis detect the swing phase and uncouple the first energy storing unit from the movement of the foot element relative to the lower leg element. In this phase the energy stored in the second energy storing unit will be released leading to a lifting of the toe of the foot. Without uncoupling of the first energy storing unit from the movement of the foot element this lifting of the foot does not occur. Especially for the case when both energy storing units comprise at least one spring element and the first energy storing unit comprises the spring with the higher stiffness this high stiffness spring element would prevent the lifting of the foot due to its high stiffness. This is also true for an embodiment in which there is no energy storing unit. In this case the lifting the foot is also prevented by the first energy storing unit because it would be loaded with energy during the lifting which will not occur without external forces. Such an embodiment is useful for patients that are able to lift the foot themselves. Since the first energy storing unit is in the swing phase by the control unit the first energy storing unit cannot lead to any resistance against the lifting of the foot. At the end of the swing phase or when the energy stored in the second energy storing unit is fully released the first energy storing unit can be recoupled to the movement of the foot element. At this point also the zero position gets reset to the angle between the foot element and the lower leg element at which this recoupling takes place. Now, a new gait cycle can start.

In another embodiment of the ankle foot orthosis the first energy storing unit is adapted such that moving the foot element relative to the lower leg element in plantarflexion direction from the first position to the second position increases the amount of energy stored in the first energy storing unit.

Compared to the embodiment of the present invention in which the movement of the foot element in plantarflexion direction leaves the amount of energy stored in the first energy storing unit unaffected as long as it is minimal this embodiment has the advantage that even more energy can be stored in the first energy storing unit. In contrast to the previously described embodiment wherein the loading of the first energy storing unit with energy starts when the controlled dorsiflexion phase begins here the loading of the first energy storing unit with energy already begins when the controlled plantarflexion phase begins. This takes place directly after the heel strike of a gait cycle.

Preferably the first energy storing unit comprises at least one pressure chamber wherein the pressure inside the pressure chamber is increased when the foot element is moved relative to the lower leg element in plantarflexion direction from the first position to the second position.

Preferably the pressure inside the pressure chamber is also increased when the foot element is moved relative to the lower leg element in dorsiflexion direction from the second position to the first position.

In a preferred embodiment of the present invention the at least one pressure chamber can be pre-pressurized. This preferably happens prior to a gait cycle, particularly in the swing phase. This enables the system to generate larger moments at the ankle compared to when no pre-pressurization is used. The initial pressure that is applied during the pre-pressurization is at least partially released during the powered plantar flexion phase.

Preferably the ankle foot orthosis comprises a hydraulic and/or pneumatic system comprising at least one cylinder in which a piston can be moved. The cylinder can be a longitudinal or circular cylinder. During the controlled plantar flexion phase and/or the controlled dorsiflexion phase the piston inside the cylinder is moved and a fluid inside the cylinder is moved into the pressure chamber. This increases the pressure inside the chamber and thus loads the energy storing unit with energy. The hydraulic and/or pneumatic system can comprise two cylinders and corresponding pistons for the controlled plantar flexion phase and the controlled dorsiflexion phase, respectively. It is also possible but not necessary to use two pressure chambers for the two different directions of movement. However both pressure chambers should release their pressure during the powered plantar flexion phase. Of course, the different pressure chambers can be individually or commonly pre-pressurized.

Using a hydraulic and/or pneumatic system allows for stepless storing of energy. No matter how large the movement of the foot relative to the lower leg is, energy will be stored in the energy storing unit. This is not necessarily the case when a ratchet mechanism is used.

In a method for controlling an ankle foot orthosis according to the present invention wherein the orthosis comprises a first uncoupling unit, this uncoupling unit is used as follows. During the complete dorsiflexion phase which directly follows the controlled plantarflexion phase the first uncoupling unit does not uncouple the first energy storing unit from the movement of the foot element. This means that the movement of the foot element relative to the lower leg element in the dorsiflexion phase leads to an increase of the amount of energy stored in the first energy storing unit. This takes place during the complete controlled dorsiflexion phase from its beginning when the maximum plantarflexion angle between the foot element and the lower leg element is reached during the gait cycle until its end when the maximum dorsiflexion angle between the foot element and the lower leg element during this gait cycle is reached. Afterwards in the powered plantarflexion phase the first uncoupling unit preferably does not uncouple the first energy storing unit from the movement of the foot element. During the swing phase the first uncoupling unit does uncouple the first energy storing unit from the movement of the foot element. In the swing phase no coupling is needed. In case there is any amount of energy stored in this phase, it will be released during the swing phase. In particular, the foot element will take its zero position relative to the lower leg element so that the next gait cycle can start with the heel strike and the following controlled plantarflexion phase.

In a preferred embodiment of this method, the first uncoupling unit uncouples the first energy storing unit from the movement of the foot element when the swing phase is detected. Preferably the orthosis comprises at least one sensor, which as an example can be a pressure sensor in the toe area of the foot orthosis. This sensor is able to detect the so-called "toe-off" which is the point the gait cycle in which the foot leaves the ground. This is the starting point of the swing phase. Once this point has been detected by the sensor an electrical or electronical control unit can be used to control the first uncoupling unit such that it uncouples the first energy storing unit from the movement of the foot element. Preferably the control unit is part of the ankle foot orthosis.

Preferably the first uncoupling unit couples the first energy storing unit to the movement of the foot element when a heel strike is detected. In order to detect this a further sensor is advantageous. It might be a pressure sensor in the heel area of the foot being able to detect the contact between the heel and the ground which is defined to be the "heel strike". Once this heel strike has been detected the first uncoupling unit is controlled such that it couples the first energy storing unit to the movement of the foot element so that the amount of energy that is stored in the first energy storing unit can be increased again.

As an alternative or additional to at least one pressure sensor several other sensors and/or combination of sensors can be used. With these usually the swing phase is to be detected. This can be achieved from acceleration variations of at least one of the foot, the shank, the thigh and the arms. Thus acceleration sensors such as gyroscopes can be used.

The at least one sensor can comprise at least one angle sensor which is capable of determining an inertial angle. When more than one of these angle sensors are used it is possible to determine the inertial angles of more than one element and to calculate from these inertial angles a relative angle between two or more elements of the angle foot orthosis. The angel sensors can be used to determine the inertial angles of at least one of the foot, the lower leg, the thigh in order to be able to calculate the angle and/or an angle variation of the ankle, the knee and/or the hip joint.

Alternatively or additionally at least one sensor can be used to register muscle activation by e.g. detected myoelectrical signals. Alternatively or additionally at least one sensor can be used to detect a centre of mass displacement of the patient. With the data obtained from at least some of these sensors it is possible to detect the swing phase of the gait cycle.

Also augmented reality can be used.

BRIEF DESCRIPTION OF THE DRAWINGS

With the enclosed figures an embodiment of the present invention will be described.

FIG. 4 shows a schematic view of an ankle foot orthosis according to another embodiment of the present invention and FIG. 5 shows an schematic view of a different embodiment of the present invention.

DETAILED DESCRIPTION

Figure 1:
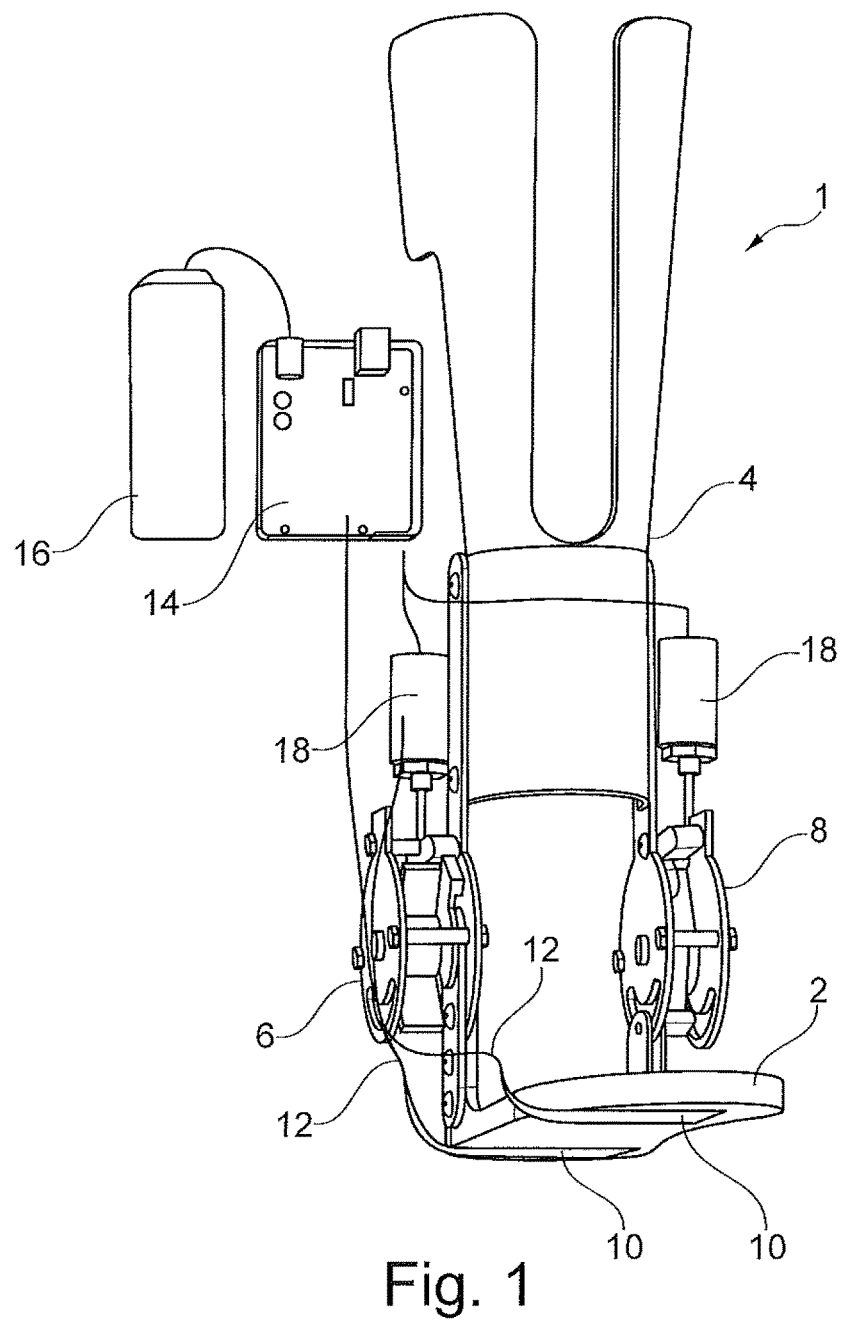
FIG. 1 shows a schematic view of an ankle foot orthosis according to one embodiment of the present invention.

FIG. 1 shows an ankle foot orthosis 1 according to a first embodiment of the present invention. It comprises a foot element 2 and a lower leg element 4. Between the foot element 2 and the lower leg element 4 there is a first joint 6 and a second joint 8.

Underneath the foot element 2 there are two pressure sensors 10 that are connected via cables 12 with an electronic control unit 14. The electronic control unit 14 is connected to a battery 16 and is adapted to send control signals to two solenoids 18. Once one of these solenoids is activated it decouples the corresponding energy storing unit, which are not shown in FIG. 1, from the corresponding joint.

Figure 2:
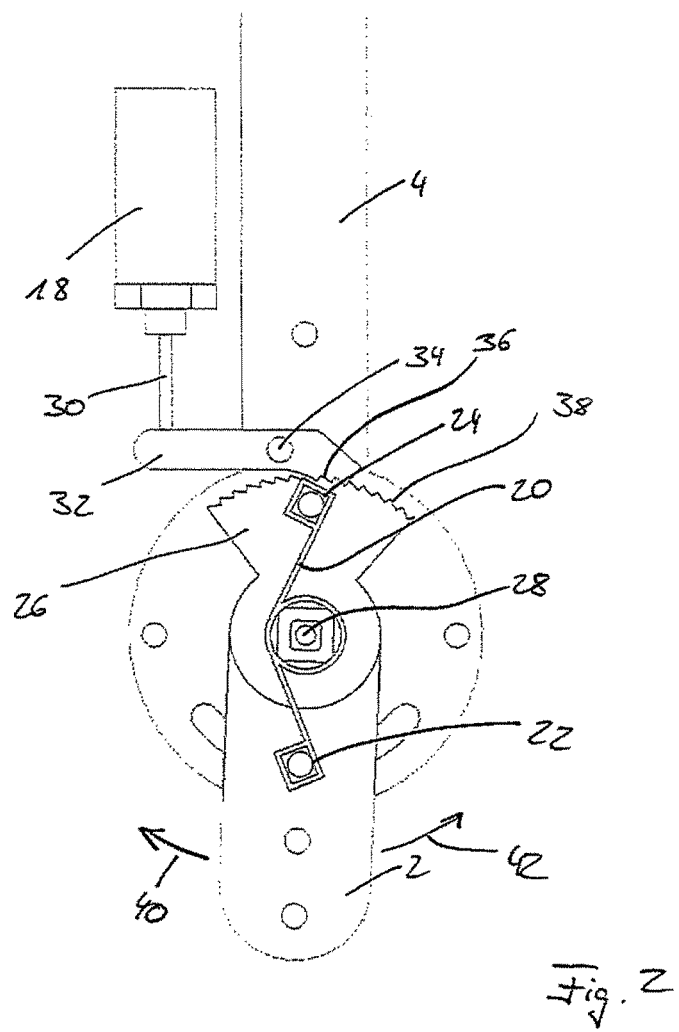
FIG. 2 shows the schematic view of a joint comprising an energy storing unit, FIG. 3 schematically shows how an ankle foot orthosis according the present invention works.

FIG. 2 shows a schematic detailed view of a joint. It is connected to the foot element 2 and the lower leg element 4 and comprises a spring element 20 which acts as the corresponding energy storing unit. The spring element 20 is connected with its first end 22 to the foot element 2 and with its second end 24 to a ratchet 26.

The foot element 2 and the lower leg element 4 are connected by the joint and can be pivoted relative to each other around a rotation axis 28.

The solenoid 18 is connected via a rod 30 to a pawl 32 which is connected pivotable around a pivot axis 34. The solenoid is connected to the lower leg element 4.

In the situation shown in FIG. 2 teeth 36 of the pawl engage the teeth 38 of the ratchet 26. FIG. 2 shows a first joint 6. In the situation shown in FIG. 2 a movement of the foot element 2 relative to the lower leg element in plantar flexion direction denoted by arrow 40 is allowed by a combination of ratchet 26 and pawl 32. Due to the special shape of the corresponding teeth this movement is allowed. In contrast, moving the foot element 2 relative to the lower leg element 4 in dorsiflexion direction which is denoted by arrow 42 is prohibited by the corresponding teeth of the ratchet 26 and the pawl 32. Moving the foot element 2 relative to the lower leg element in the direction of arrow 42 leads to a tensioning of the spring element 20 and thus to a loading of the corresponding energy storing unit.

Figure 3:
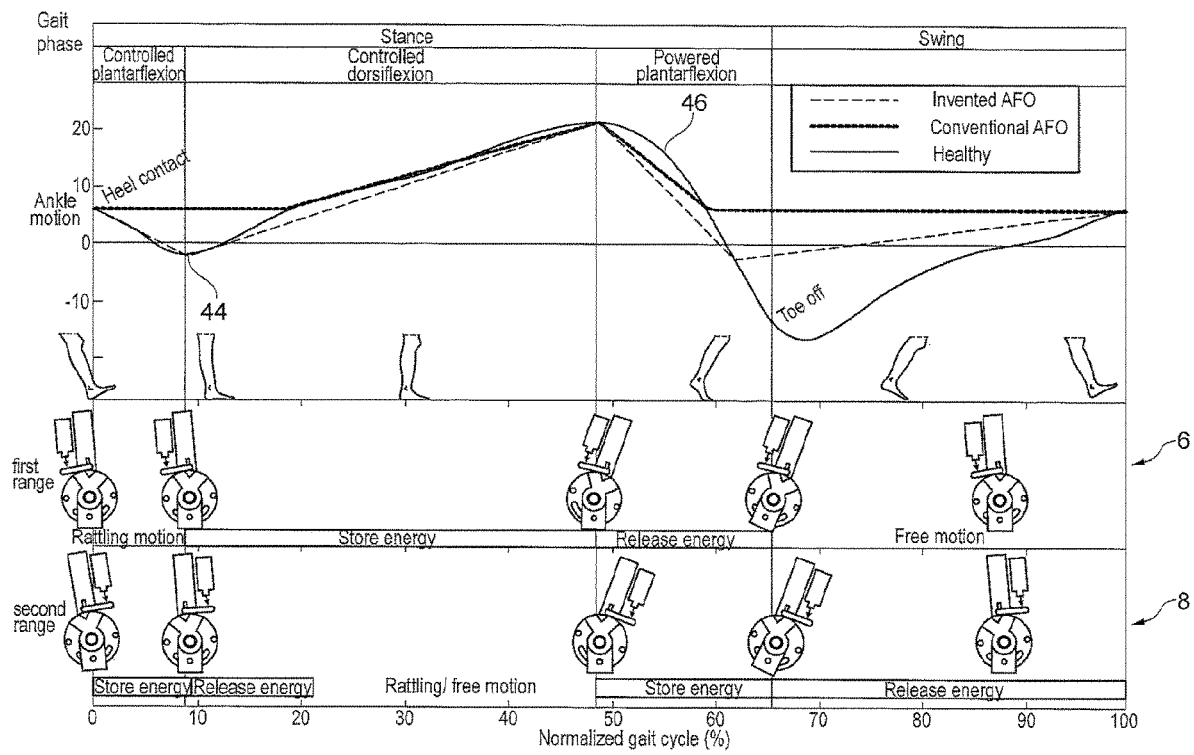

FIG. 3 schematically shows a gait cycle. The full line shows a typical gait cycle of a healthy person. With the dashed line the movement of the ankle foot orthosis according to an embodiment of the present application is shown. First at the beginning of the controlled plantar flexion phase the heel is set onto the floor. Afterwards the controlled plantar flexion phase starts. Here the foot element 2 is moved relative to the lower leg element in plantar flexion direction. This means that the first neutral setting of the first joint gets shifted towards plantar flexion direction to the point indicated with reference 44. At the same time the second energy storing unit stores energy.

Afterwards the controlled dorsiflexion phase begins until the maximum dorsiflexion point denoted with reference number 46. This point indicates the end of the controlled dorsiflexion phase. At the beginning of this phase the energy stored in the second energy storing unit is released while the first energy storing unit gets loaded with energy. Afterwards in the powered plantar flexion phase the energy stored in the first energy storing unit is released again until the swing phase starts. In the swing phase advantageously the first energy storing unit is uncoupled from the first joint so that the energy stored in the second energy storing unit can be released leading to a lifting of the toe.

The dotted line denotes the movement of an orthosis according to the prior art. In the lower parts of FIG. 3 it is shown how the first joint 6 and the second joint 8 act in the different phases of the gait. When then pawl 32 engages the teeth 38 of the ratchet 26 energy can be stored in or released from the energy storing unit.

Figure 4:
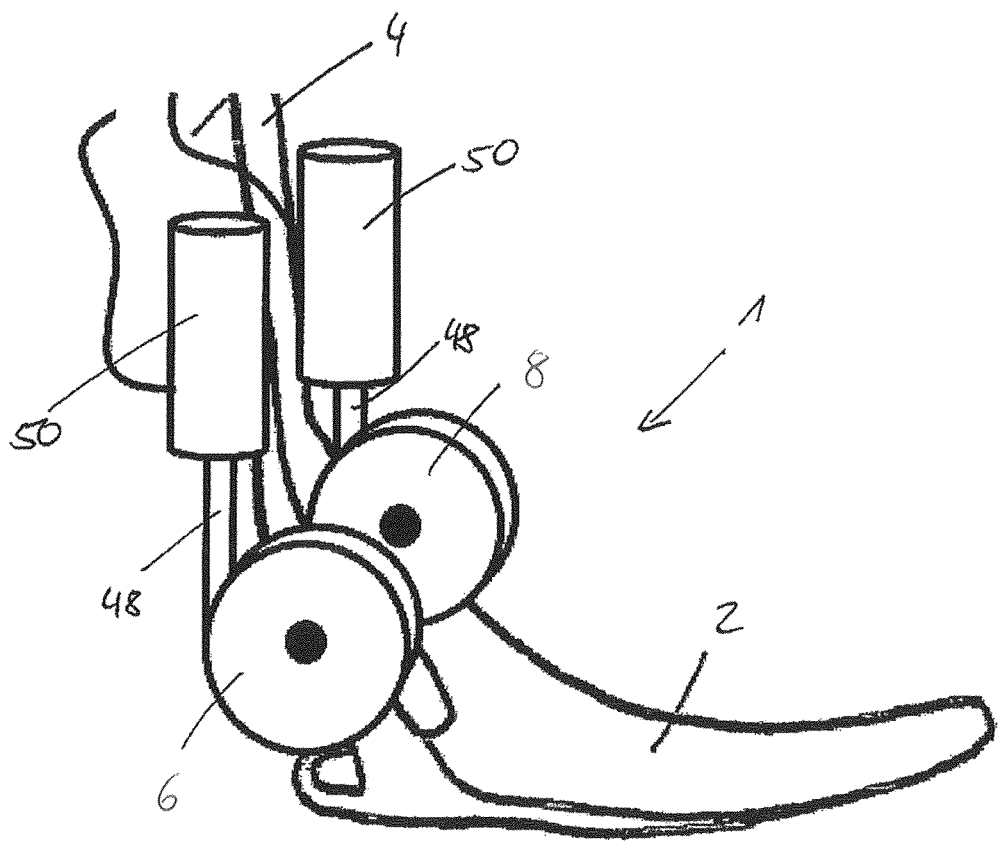

FIG. 4 shows another embodiment of the present application. The ankle foot orthosis 1 comprises a foot element 2 and a lower leg element 4. There is a first joint 6 and a second joint 8. In contrast to the embodiment shown in FIGS. 1 and 2 there are no spring elements acting as energy storing units. In contrast there is a high drawl existent comprising tubes 48 and two pressure reservoirs 50 that act as energy storing units.

FIG. 5 shows a different embodiment of the present invention. It comprises a pressure chamber 52 which is on its left side connected to a heel cylinder 54 which is shown in an enlarged view in the top part of FIG. 5. On the right side of the heel cylinder there are two valves 56 which open under pressure while on the left side of the heel cylinder 54 there are two valves 58 opening due to suction. Inside the heel cylinder 54 there is a piston 60 which is coupled by a rod 62 to the heel part 64 of the foot element 2.

At the heel part 64 of foot element 2 there is a pressure sensor 10. The pressure chamber 52 is coupled to a forefoot cylinder 66 via a tube 68. At the connection between the tube 68 and the pressure chamber 52 there is an electric valve 70. The electric valve 70 is opened when there is no pressure measured by the pressure sensor 10. The electric valve 70 is closed when the pressure sensor 10 detects a pressure.

A piston 60 inside the forefoot cylinder 66 is biased by a spring 72. On top of the pressure chamber 52 there is a cover 74 carrying a battery 76 and a micro controller 78.

During heel strike the pressure sensor 10 detects a pressure so that the electric valve 70 is closed. The valve stays closed as long as the heel part 64 of the foot element 2 is in contact with the ground. During controlled plantarflexion phase and controlled dorsiflexion phase the piston 60 is moved up and down inside the heel cylinder 54 thereby increasing the pressure inside the pressure chamber 52. In the plantarflexion phase the spring 72 is compressed. It relaxes in the first part of the controlled dorsiflexion phase and gets elongated until the maximum dorsiflexion angle at the end of the controlled dorsiflexion phase is reached.

When the heel leaves the ground the pressure sensor 10 does not detect any pressure anymore so that the electric valve 70 opens. Inside the pressure chamber 52 there is a high pressure which is now released through the tube 68 into the forefoot cylinder 66 thereby pushing the piston 60 inside the forefoot cylinder 66 downwards. This leads to a powered plantarflexion phase and to a compression of the spring 72. Once the pressure inside the pneumatic system and in particular inside the pressure chamber 52 is released and the toe leaves the ground the spring 72 relaxes and lifts the toe area of the foot element 2 in the swing phase.

REFERENCE LIST 1 ankle foot orthosis
2 foot element
4 lower leg element
6 first joint
8 second joint
10 pressure sensor
12 cable
14 electronic control unit
16 battery
18 solenoid
20 spring element
22 first end
24 second end
26 ratchet
28 rotation axis
30 rod
32 pawl
34 pivot axis
36 teeth
38 teeth
40 arrow
42 arrow
44 maximum plantar flexion angle at the end of controlled plantarflexion phase
46 maximum dorsiflexion angle at the end of controlled dorsiflexion phase
48 tube
50 pressure reservoir
52 pressure chamber
54 heel cylinder
56 valve opening under pressure
58 valve opening due to suction
60 piston
62 rod
64 heel part
66 forefoot cylinder
68 tube
70 electric valve
72 spring
74 cover
76 battery
78 micro controller

The invention claimed is:

1. An ankle foot orthosis comprising:
a lower leg element;
a foot element being pivotably coupled to the lower leg element around a pivot axis;
a first energy storing unit being adapted such that moving the foot element relative to the lower leg element in a dorsiflexion direction from a position in which an amount of energy stored in the first energy storing unit is minimal loads the first energy storing unit with energy;
wherein the first energy storing unit is adapted such that the amount of energy stored in the first energy storing unit is increased by:
first moving the foot element relative to the lower leg element in a plantar flexion direction from a first position in which the amount of energy stored in the first energy storing unit is minimal into a second position; and afterwards moving the foot element relative to the lower leg element in the dorsiflexion direction from the second position back into the first position; and a second energy storing unit adapted such that moving the foot element relative to the lower leg element in the plantar flexion direction from a position in which the amount of energy stored in the second energy storing unit is minimal loads the second energy storing unit with energy, wherein each of the first and second energy storage units includes at least one spring element, and wherein the at least one spring element of the first energy storing unit has a higher stiffness than a stiffness of the at least one spring element of the second energy storing unit.

2. The ankle foot orthosis according to claim 1, wherein the first energy storing unit is adapted such that the amount of energy stored in the first energy storing unit after the foot element is moved from the first position into the second position is still minimal.

3. The ankle foot orthosis according to claim 1, wherein the second energy storing unit is adapted such that moving the foot element relative to the lower leg element in the dorsiflexion direction from a position in which the amount of energy stored in the second energy storing unit is minimal does not change the amount of energy stored in the second energy storing unit.

4. The ankle foot orthosis according to claim 1, further comprising a first uncoupling unit adapted to uncouple the first energy storing unit from movement of the foot element relative to the lower leg element, such that moving the foot element relative to the lower leg element does neither load nor unload the first energy storing unit, wherein the first energy storing unit is adapted to release the stored energy when the first uncoupling unit uncouples the first energy storing unit.

5. The ankle foot orthosis according to claim 4, further comprising at least one sensor to identify a swing phase of a gait cycle at a control unit to uncouple the first energy storing unit from the movement of the foot element relative to the lower leg element when a swing phase is identified.

6. The ankle foot orthosis according to claim 5, wherein the at least one sensor includes two pressure sensors.

7. The ankle foot orthosis according to claim 1, further comprising a second uncoupling unit adapted to uncouple the second energy storing unit from the movement of the foot element relative to the lower leg element, such that moving the foot element relative to the lower leg element does neither load nor unload the second energy storing unit, wherein the second energy storing unit is adapted to release the stored energy when the second uncoupling unit uncouples the second energy storing unit.

8. The ankle foot orthosis according to claim 7, wherein at least one of the first uncoupling unit and the second uncoupling unit comprises a pawl and a ratchet.

9. The ankle foot orthosis according to claim 1, wherein at least one of the first energy storing unit and the second energy storing unit comprises at least one spring element.

10. The ankle foot orthosis according to claim 1, wherein the first energy storing unit is adapted such that moving the foot element relative to the lower leg element in the plantar flexion direction from the first position to the second position increases the amount of energy stored in the first energy storing unit.

11. A method for controlling an ankle foot orthosis comprising:

providing the ankle foot orthosis with a lower leg element, a first uncoupling unit, a foot element pivotably coupled to the lower leg element around a pivot axis, a first energy storing unit adapted such that moving the foot element relative to the lower leg element in a dorsiflexion direction from a position in which an amount of energy stored in the first energy storing unit is minimal loads the first energy storing unit with energy, wherein the first energy storing unit is adapted such that the amount of energy stored in the first energy storing unit is increased by first moving the foot element relative to the lower leg element in a plantar flexion direction from a first position in which the amount of energy stored in the first energy storing unit is minimal into a second position, and afterwards moving the foot element relative to the lower leg element in the dorsiflexion direction from the second position back into the first position, and a second energy storing unit adapted such that moving the foot element relative to the lower leg element in the plantar flexion direction from a position in which the amount of energy stored in the second energy storing unit is minimal loads the second energy storing unit with energy, wherein each of the first and second energy storage units includes at least one spring element, and wherein the at least one spring element of the first energy storing unit has a higher stiffness than a stiffness of the at least one spring element of the second energy storing unit;

during a complete controlled dorsiflexion phase of a gait cycle the first uncoupling unit does not uncouple the first energy storing unit from the movement of the foot element so that the amount of energy stored in the first energy storing unit increases; and during a swing phase of the gait cycle the first uncoupling unit does uncouple the first energy storing unit from the movement of the foot element.

12. The method according to claim 11, wherein the first uncoupling unit uncouples the first energy storing unit from movement of the foot element when the swing phase is detected.

13. The method according to claim 11, wherein the first uncoupling unit couples the first energy storing unit to movement of the foot element when a heel strike is detected.

14. An ankle foot orthosis comprising:
a lower leg element;
a foot element pivotably coupled to the lower leg element;
a first energy storing unit storing additional energy in response to:
moving the foot element relative to the lower leg element in a plantar flexion direction from a first position in which an amount of energy already stored in the first energy storing unit is at a minimum amount into a second position and moving the foot element relative to the lower leg element in a dorsiflexion direction from the second position back into the first position; and
a second energy storing unit adapted such that moving the foot element relative to the lower leg element in the plantar flexion direction from a position in which the amount of energy stored in the second energy storing unit is minimal loads the second energy storing unit with energy, wherein each of the first and second energy storage units includes at least one spring element, and wherein the at least one spring element of the first energy storing unit has a higher stiffness than a stiffness of the at least one spring element of the second energy storing unit.

\* \* \* \* \*